United States Patent [19]

Mukerji

[11] Patent Number: 4,502,699
[45] Date of Patent: Mar. 5, 1985

[54] ROTATING SEAL FOR CONTINUOUS FLOW CENTRIFUGE

[75] Inventor: Sushim Mukerji, Newark, Del.

[73] Assignee: E. I. Du Pont de Nemours and Company, Wilmington, Del.

[21] Appl. No.: 494,976

[22] Filed: May 16, 1983

[51] Int. Cl.³ .............................................. B04B 11/00
[52] U.S. Cl. .......................................... 277/74; 494/41
[58] Field of Search .................... 277/59, 74; 209/155; 494/41, 14

[56] References Cited

U.S. PATENT DOCUMENTS

| | | | |
|---|---|---|---|
| 3,443,747 | 5/1969 | Jacobson et al. | 277/59 |
| 4,011,972 | 3/1977 | Pederson et al. | 233/1 |
| 4,357,235 | 11/1982 | Dilks, Jr. | 201/1 |
| 4,375,871 | 3/1983 | Romanauskas | 277/74 |

FOREIGN PATENT DOCUMENTS 1910576 3/1969 Fed. Rep. of Germany .
925677 2/1962 United Kingdom .

Primary Examiner—Robert I. Smith

[57] ABSTRACT

A rotating seal assembly for a continuous flow centrifuge is described. The seal assembly permits both elements of the rotating seal, the rotating member as well as a nonrotating member to be resiliently mounted and in such a manner that both may rock as necessary to accommodate the vibrations of the other. Furthermore, the drive for the rotating member is decoupled so that greater freedom of movement for the rotating member is afforded.

10 Claims, 3 Drawing Figures

ROTATING SEAL FOR CONTINUOUS FLOW CENTRIFUGE

BACKGROUND OF THE INVENTION

This invention relates to rotating seals for continuous flow type centrifuges.

Continuous flow centrifuges provide a continuous flow of fluid into and out of a spinning rotor. This is accomplished by the use of rotating face seals having a rotating member and a nonrotating member in face-to-face contact. While simple in theory, many problems have been encountered with the rotating seals because of their tendency to leak particularly at high speeds. The causes of these leaks are manifold. For one, the rotating member, being connected to the centrifuge rotor, causes the nonrotating member to toss resulting in a separation of the members and leakage at the seal. Such leakage also is caused by misalignment induced vibrations between the faces of the two members and the inability of the two members to track the motion of each other. Additional pressure between the members does not always help. If too much pressure is applied there is undue wear of the seal faces and consequent leakage of the seal.

A number of efforts have been made in the prior art to correct these problems. Thus Jacobson et al. in U.S. Pat. No. 3,443,747 propose the use of a rotating member made of a very hard material with the stationary member being contructed of a tetrafluoroethylene polymer and being vertically movable to accommodate some movement of the rotating element. German Auslegundschrift No. 1,910,576 teaches the use of the seal members made respectively of titanium and fiberglass reinforced plastic. Since both materials have about the same thermal coefficient of expansion alignment problems are reduced. The stationary member is spring loaded against a horizontally movable plate to facilitate its accommodating the transverse movements of the rotary member.

British Pat. No. 925,677 describes a stationary member which is spring loaded against a rotating member, the rotating member being cushion mounted. U.S. Pat. No. 4,011,972, issued to Pederson et al. permits axial movement of the spindle for the stationary seal. Dilks in U.S. Pat. No. 4,357,235 uses a flexible shaft to drive the rotating member. Both members of the seal are mounted on a gasket to facilitate their accommodating the motion of one another. Finally, Romanauskas in his U.S. Pat. No. 4,375,871 positions the rotating seal at the center of mass of the rotor to reduce its vibration and uses a three point spring mounting for the stationary member.

All of these efforts of the prior art have tended to reduce the leakage through the rotating seals of continuous flow centrifuges, many to a significant extent. Many of these approaches, however, tend to encounter difficulty and leak as the rotating speed of the centrifuge is increased above 10,000 rpm. Another problem encountered when the centrifuge is to be used in sedimentation field flow fractionation applications is that it is difficult to maintain alignment of the small diameter flow channels required. The channels must remain relatively small to prevent band broadening in the separation.

SUMMARY OF THE INVENTION

A rotating seal is constructed for a continuous flow centrifuge which facilitates relatively leak free operation of the centrifuge even at relatively high speeds. The centrifuge has a rotor which is mounted on a drive shaft for rotation within a housing about the axis of the drive shaft, a rotating face seal assembly having interengaged rotating and nonrotating members for conveying fluids to and from the rotor, the members each having corresponding communicating passages for conveying the fluids. The centrifuge is improved by flexibly mounting the seal assembly to the housing to permit both axial and transaxial movement of the seal assembly. The flexible mounting includes a rubber sheet whose periphery is secured to the housing and interior is secured to the seal assembly. In this manner the seal assembly can better accommodate itself to the motions of the centrifuge rotor.

Within the seal assembly, a spring means is positioned to bias the nonrotating member along the axis of rotation toward the rotating member so that the stationary member can better follow the movements of the rotating member. A resilient means is used to both mount and rotate the rotating member. The resilient means includes a rotating base coupled to rotate with the rotor and a flat resilient gasket, the rotating member and base of each having an opposed pin engaging only the gasket. In this manner the gasket decouples the rotating member from the eccentricities of the rotation of the base. Fewer of the vibratory motions of the rotor are transmitted to the rotating member which facilitates its remaining engaged against the nonrotating member.

Finally the rotating member has a contacting and noncontacting face, relative to the nonrotating member, with the noncontacting face being stepped. This facilitates a rocking movement of the rotating member to better track movements of the face of the nonrotating member. The contacting face of the rotating member defines an outer annular groove to reduce friction and has an outer ring to increase outer radial contact with the nonrotating member and hence enhance the stability of the facial contact.

These features permit the rotating member and the stationary member to track the movements of each other with their mating faces remaining in contact even though either or both can undergo significant vibratory movements due to the motion of the system. Relatively high speeds up to 20,000 rpm can be achieved without significant seal leakage. Further, alignment of the narrow flow channels within the two members is greatly improved.

BRIEF DESCRIPTION OF THE DRAWINGS

Further advantages and features of this invention will become apparent from the following description wherein.

DETAILED DESCRIPTION OF THE PREFERRED EMBODIMENT

Figure 1:
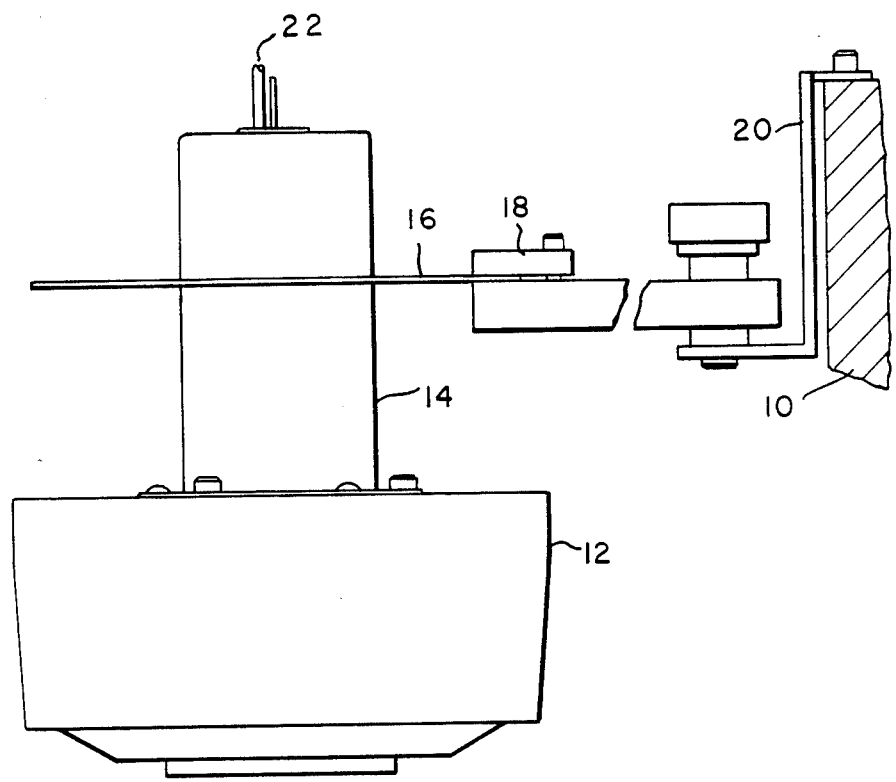
FIG. 1 is a partial elevation view of a continuous flow centrifuge in which the rotating seal of this invention finds use.

There may be seen in FIG. 1 a continuous flow type centrifuge mounted in a housing 10. The centrifuge includes a bowl type rotor 12 which, a in typical application, can house a sedimentation field flow fractionation channel of the type described, for example, in Dilks, U.S. Pat. No. 4,357,235. The rotor 12 may be one of conventional design such as the TZ-28 rotor sold by E. I. du Pont de Nemours and Company, Wilmington, Del. The TZ-28 rotor has a raised center portion 24 (FIG. 2) which accommodates the drive spindle of a centrifuge. A rotating seal assembly 14 is rotatably secured to the top center portion of the rotor 12 to facilitate the transfer of fluids to and from the rotor 12. The seal assembly 14 is flexibly mounted, in accordance with this invention, to the housing 10 by a resilient sheet 16. In this instance the flexible mounting 16 may be in the form of an annular ring formed of a rubber or other resilient material. This flexible mounting 16 permits the rotating seal assembly 14 to accommodate itself to the vibrations of the rotor 12 to reduce leakage of the rotating seal itself. The outer peripheral portion of the resilient sheet 16 is secured by upper and lower ring brackets 18 and thence to the sidewall of the housing 10 by an additional bracket 20. Tubes 22, for passing the fluid to and from the rotor, may be seen at the top center of the assembly 14 in the illustration.

Figure 2:
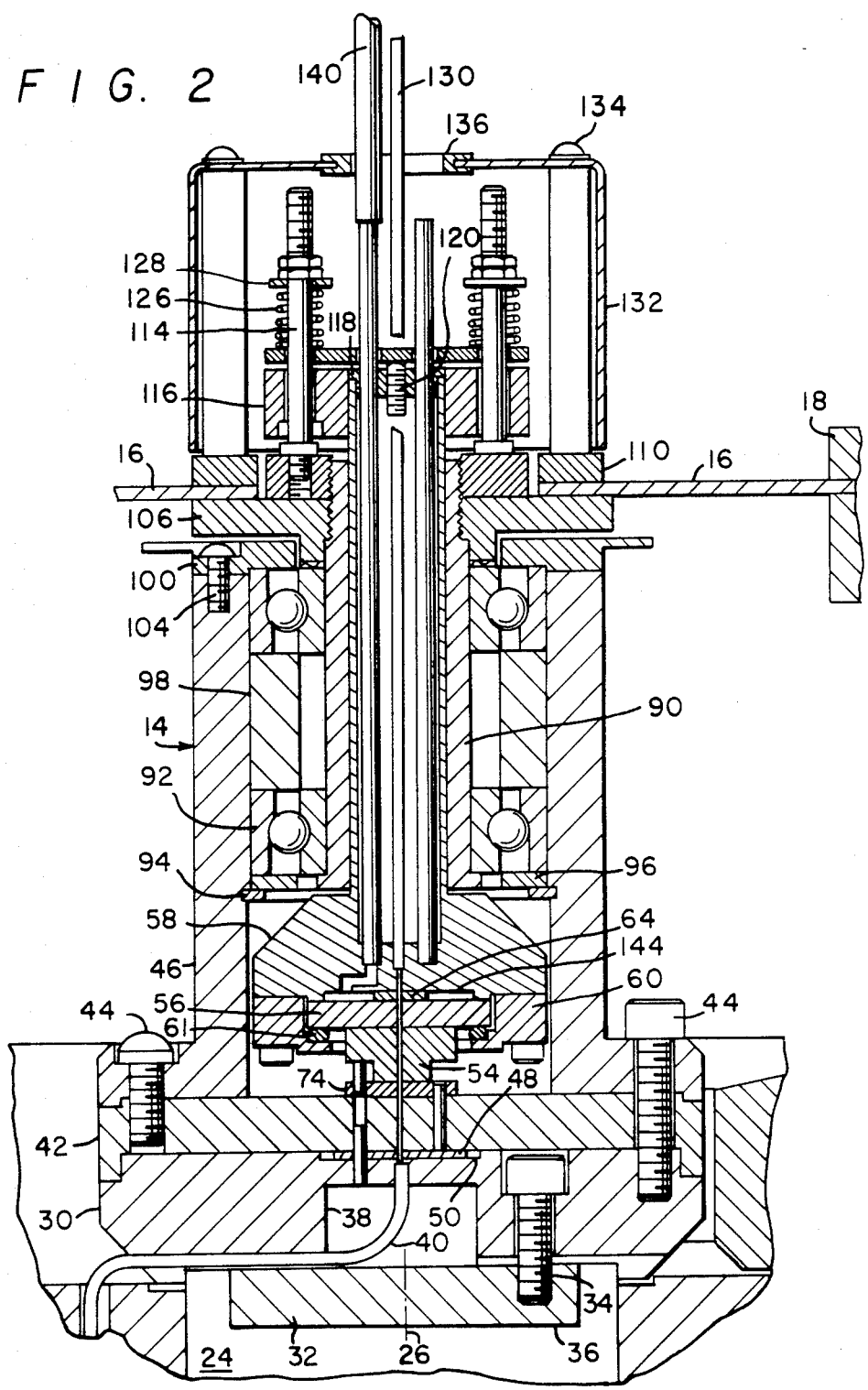
FIG. 2 is a cross section elevation view of the rotating seal assembly used in the centrifuge of FIG. 1.

The construction of the rotating seal assembly 14 is best seen in FIG. 2. There may be seen at the bottom center of the figure, a raised portion 24 of the bowl type centrifuge rotor 12 seen in FIG. 1. The bottom portion of the rotating seal assembly 14 is adapted to sit on the top of the raised center portion 24 and rotates with the rotor itself along the axis of rotation 26 of the rotor. The seal assembly includes a rotating lower portion and a nonrotating upper portion to which the fluid transport 130 and cooling water 140 tubes are connected.

The rotating portion of the seal assembly includes a base plate 30 secured to a retainer plate 32 as by screws 34 and adapted to fit within a central recess portion 36 at the top of the raised portion 24 of the centrifuge rotor 12. This bottom retainer plate 32 and base plate 30 of course may be modified to permit the use of the seal assembly with other types of continuous flow rotors. The central bottom portion 38 of the base plate 30 is recessed and the bottom portion thereof grooved to accommodate tubes 40 for the passage of fluids to and from the rotating seal into the rotor.

An intermediate base plate 42 with a downwardly extending ring flange fits over the base plate 30. A cylindrical bearing housing 46 is secured on the top side of the intermediate base plate 42 by screws 44. Some of the screws 44 secure the bearing housing 46 only to the intermediate plate 42. A lower resilient gasket 48 is positioned in a recess 50 formed in the top center portion of the base plate 30 to provide channels for the fluids flowing through the rotating seal. These channels are in alignment with similar channels formed in the intermediate plate 42.

In accordance with this invention the rotating seal assembly is constructed of a lower rotating member 54 which forms a rotating face seal and an upper nonrotating member 56 which forms a stationary face seal. The nonrotating member 56 is positioned at the lower or head end of a stationary spindle 58 which, as will be described, is vertically moveable and spring biased downwardly so that the nonrotating member 56 engages tightly the rotating member 54. The nonrotating member 56 is housed at the lower end of the spindle 58 by a seal retainer 60 which clamps the peripheral edge of the nonrotating member 56 between an O-ring 61 and the lower end of the spindle 58. An upper gasket, 64 which is resilient, is positioned between the mid-portion of the nonrotating member 56 and the central portion of the spindle 58. Both the upper gasket 64 and the nonrotating member 56 have central and offset bores formed therein to provide channels for the fluid passing to and from the rotor.

Figure 3:
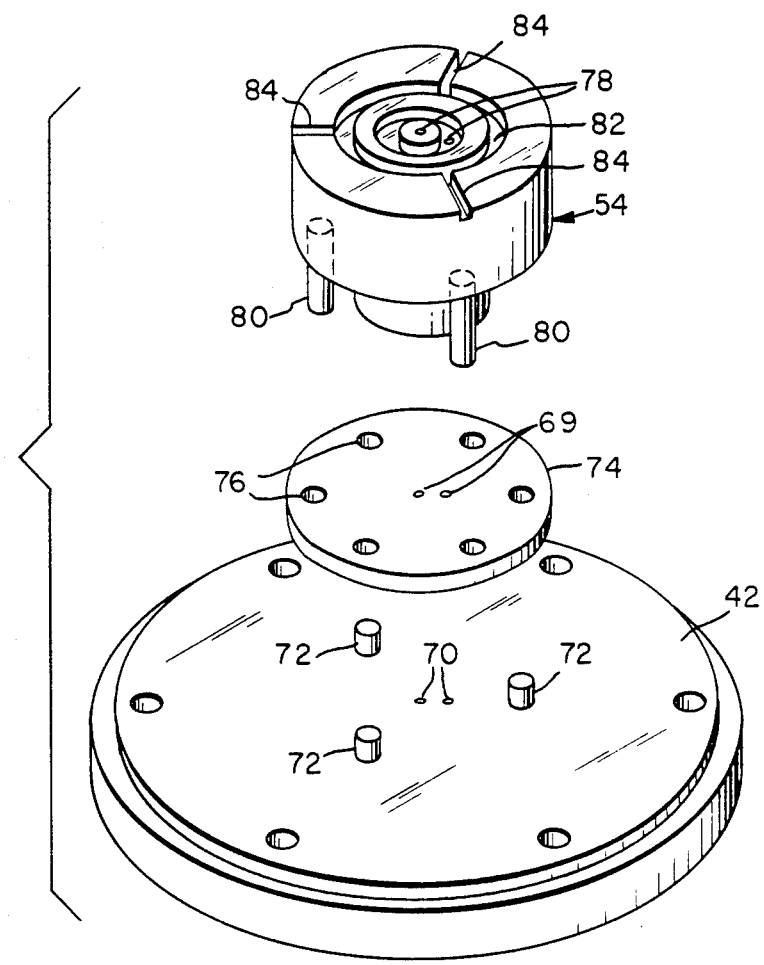
FIG. 3 is an exploded pictorial view of the rotating member depicting the resilient gasket drive mechanism that is used in the rotating seal of FIG. 2.

The particular structure of the rotating member 54 and the manner in which it is mounted in accordance with this invention is best seen with reference to FIG. 3. In this figure there is seen the intermediate plate 42 having central and offset bores 70 formed therein for the fluid lines. Additionally three equi-distant, circumferentially spaced pins 72 extend upwardly a distance slightly less than the thickness of the resilient gasket 74 positioned between the intermediate plate 42 and rotating member 54. Alternate holes 76 in the gasket are engaged by the pins 72. In like manner, the rotating member 54 is formed with the bottom portion stepped to engage the central portion of the top of the resilient gasket 74. Central and offset bores 78 are formed in the rotating member 54 with the offset bore in an annular groove located to communicate with the bores in the nonrotating member 56. Similarly, central and offset bores 69 are aligned with the bores 70 in the plate 42. Circumferentially spaced pins 80 extend downwardly from the member 54 to engage the remaining three holes in the gasket 74. These pins extend a distance below the bottom of the member 54 to a distance less than the thickness of the gasket 74. The top or sealing face of the member 54 is formed with an outer peripheral groove 82 to reduce the surface contact with the nonrotating member 56 and yet provide stability because of the peripheral raised portion 83. Radial grooves 84 are formed to permit gasses to escape from the groove 82.

With this construction it is seen that the drive for the rotating member 54 is through the resilient gasket 74 with no rigid contact therebetween. This together with the reduced area of contact with the rotating member 54 permits the member 54 to rock to the extent necessary to accommodate itself to and maintain full contact with the seal face of the nonrotating member 56 (FIG. 2). The wide top face of the member 54 helps to insure good contact between the face seals with reduced rocking therebetween and thereby reduced leakage.

The rotating member 54 may be formed of a soft, resilient material such as carbon graphite or a synthetic material sold under the trademark Feurlonc by the Rogers Corporation, Georgia. The nonrotating member 56 is formed of a harder material such as tungsten carbide. Suitable materials of this type may be purchased under the trademark Carboloy 883 from General Electric Company or Kennmetal K68. Alternatively, silicon carbide materials may be used for the member 56. Whatever the material used, both seal forces should be polished to have an extremely smooth surface and have a surface flatness to within one wavelength of light. The various gaskets 64, 74 and 50 may be formed of any suitable material such as silicone rubber or natural rubber.

To complete the description of the assembly 14, the spindle 58 is held and permitted to slide vertically along the axis 26 by a bearing preload tube 90. Bearings 92 are positioned along the preload tube and held by a lower retaining ring 94, a bearing spacer 96, a second bearing spacer 98 between the bearings 92, a wave washer 101, and a bearing cap assembly 100, which is secured to the bearing assembly 46 as by screws 104. This completes the description of the rotating portion of the seal assembly.

Continuing upward in the drawing of FIG. 2, a preload tube nut 106 is threaded onto the top portion of the bearing preload tube 90. The annular resilient support 16 rests on the top of the preload tube nut 106. A clamping ring 110 clamps the support 16 against the preload tube nut 106, thus resiliently securing the stationary portion of the rotating seal assembly to the housing 10 (FIG. 1). A lock nut 112, also secured to the top of the preload tube 90, insures a secure assembly.

Spring posts 114 are positioned around portions of the circumference of the lock nut 112 and serve as guides for a spindle clamp 116. The spindle clamp 116 slides along the spring posts and engages the top portion of the spindle 58. A spindle cap 118 fits over the top portion of the spindle 58. An oval point set screw 120 is threaded in the spindle cap 118 and engages a pressure plate 124 which slides on the spring posts 114. The pressure plate 124 is preloaded by springs 126 on the spring posts 114 held by a spring retainer 128. Conduits in the form of stainless steel tubes 130 pass down through bores in the spindle 50 to the spindle cap 118 and spindle 58 thence through bores in the spindle 50 to the stationary face seal of the nonrotating member 56. A cover 132 may be secured to the lock nut 112 as by screws 134. The central portion of the cover is open as at 136 to accommodate the conduits 130. In addition, water or other cooling fluid lines 140 pass downwardly through the pressure plate 124 and spindle 58, through bores 142 in the head end of the spindle 58 to pass fluid into the annular region 144 between the nonrotating member 56, the cavity of the spindle 58, and the gasket 64.

There has thus been described a unique rotating seal assembly in which the rotating member of the seal is sufficiently resilient mounted so that it maintains close sealing contact with the nonmoving face seal at all times during operation and at relatively high speeds.

I claim:

1. In a continuous flow centrifugal apparatus having a housing and a rotor mounted on a drive shaft for rotation within said housing about the axis of said drive shaft, and a rotating seal assembly having interengaged rotating and nonrotating members for conveying fluids to and from said rotor, said members each having corresponding communicating passages for conveying said fluids, the improvement wherein said assembly is flexibly mounted to said housing to permit axial and transaxial movement of said assembly where said flexible mounting includes a resilient sheet whose periphery is secured to the housing and whose interior is secured to the seal assembly.

2. The apparatus of claim 1 wherein said assembly is mounted by an annular rubber sheet.

3. The apparatus of claim 2 which includes the further improvement of spring means to bias the nonrotating member along the axis of rotation toward the rotating member.

4. The apparatus of claim 1 which includes the further improvement of spring means to bias the nonrotating member along the axis of rotation toward the rotating member.

5. In a continuous flow centrifugal apparatus having a housing and a rotor mounted on a drive shaft for rotation within said housing about the axis of said drive shaft, and a rotating seal assembly having interengaged rotating and nonrotating members for conveying fluids to and from said rotor, said members each having corresponding communicating passages for conveying said fluids, the improvement wherein said assembly is flexibly mounted to said housing to permit axial and transaxial movement of said assembly, said flexible mounting includes a resilient sheet whose periphery is secured to the housing and the interior is secured to the seal assembly, resilient means for mounting and rotating the rotating member, and wherein the resilient mounting means includes a rotating base coupled to rotate with the rotor and a flat, resilient gasket, the rotating member and base each having an opposed, offset pin engaging only the gasket, whereby the gasket couples the rotating member to be rotated by the base.

6. The apparatus of claim 6 where the base and rotating member each have three opposed, nonengaging pins coupled to said gasket.

7. The apparatus fo claim 5 which includes the further improvement of spring means to bias the nonrotating member along the axis of rotation toward the rotating member.

8. The apparatus of claim 1 which includes the further improvement of the rotating member having a contacting and noncontacting face relative to the nonrotating member, the noncontacting face being stepped to facilitate rocking of the rotating member.

9. The apparatus of claim 8 wherein said assembly is mounted by an annular rubber sheet peripherally secured to said housing.

10. In a continuous flow centrifugal apparatus having a housing and a rotor mounted on a drive shaft for rotation within said housing about the axis of said drive shaft, and a rotating seal assembly having interengaged rotating and nonrotating members for conveying fluids to and from said rotor, said members each having corresponding communicating passages for conveying said fluids, the improvement wherein said assembly is flexibly mounted to said housing to permit axial and transaxial movement of said assembly, said rotating member having a contacting and noncontacting face relative to the nonrotating member, the noncontacting face being stepped to facilitate rocking of the rotating members, the resilient mounting means including a rotating base coupled to rotate with the rotor and a flat, resilient gasket, the rotating member and base each having an opposed, offset pin engaging only the gasket, whereby the gasket couples the rotating member to be rotated by the base.

* * * * *